United States Patent [19]

Gordon et al.

[11] Patent Number: 5,556,406
[45] Date of Patent: Sep. 17, 1996

[54] CORNEAL TEMPLATE AND SURGICAL PROCEDURE FOR REFRACTIVE VISION CORRECTION

[75] Inventors: Eugene I. Gordon, Mountainside; Peretz Feder, Englewood; M. Ekramul H. Khan, Newark, all of N.J.

[73] Assignee: Medjet Inc., Edison, N.J.

[21] Appl. No.: 304,245

[22] Filed: Sep. 12, 1994

[51] Int. Cl.⁶ .................................................. A61B 17/32
[52] U.S. Cl. ............... 606/166; 606/1; 606/167; 606/174; 604/22
[58] Field of Search .................. 606/4–6, 1, 10–18, 606/166, 167, 174; 604/20–22

[56] References Cited

U.S. PATENT DOCUMENTS

| | | |
|---|---|---|
| 3,818,913 | 6/1974 | Wallach .................................. 604/28 |
| 4,205,682 | 6/1980 | Crock et al. . |
| 4,406,285 | 9/1983 | Villasenor et al. . |
| 4,526,171 | 7/1985 | Schachar . |
| 4,619,259 | 10/1986 | Graybill et al. . |
| 4,660,556 | 4/1987 | Swinger et al. . |
| 4,665,914 | 5/1987 | Tanne . |
| 4,668,570 | 8/1987 | Kramer et al. . |
| 4,705,037 | 11/1987 | Peyman et al. . |
| 4,796,623 | 1/1989 | Krasner et al. . |
| 4,903,695 | 2/1990 | Warner et al. .................................. 606/4 |
| 4,905,711 | 3/1990 | Bennett . |
| 5,074,862 | 12/1991 | Rausis .................................. 606/10 |
| 5,092,863 | 3/1992 | Schanzlin .................................. 606/5 |
| 5,108,412 | 4/1992 | Krumeich et al. . |
| 5,226,905 | 7/1993 | Hanna . |
| 5,336,215 | 8/1994 | Hseuh . |

FOREIGN PATENT DOCUMENTS 9404844  5/1994  WIPO .................................. 606/4

*Primary Examiner*—David Shay
*Attorney, Agent, or Firm*—Graham & James LLP

[57] ABSTRACT

A method for the selective removal of corneal tissue, and change of curvature thereof, for refractive vision correction, by means of a correction template in conjunction with a planar cutting high pressure water jet micro-keratome. The correction template is adapted to provide a planar cutting guide, on the corneal tissue, for the refractive correction required, with the template being shaped with a non-planar surface of predetermined configuration (related to the desired correction). The non-planar surface of the template is fitted to the area of the cornea to be refractively corrected, whereby the corneal tissue to be removed is selectively deformed so as to be substantially conformed to and held against the non-planar surface. Application of a vacuum between the template and cornea aids in this holding. The water jet micro-keratome, in a sheet-like configuration provides a full non-scanning transverse planar cut through the corneal tissue at a position adjacent the template, such that release of the template from the corneal tissue results in the undeformed configuration thereof having the desired correction. Use of the water jet micro-keratome provides a cut corneal tissue surface of smoothness and polish, substantially equivalent to that of the original surface.

25 Claims, 5 Drawing Sheets

5,556,406

CORNEAL TEMPLATE AND SURGICAL PROCEDURE FOR REFRACTIVE VISION CORRECTION

FIELD OF THE INVENTION

This invention relates to methods and devices utilized in surgical procedures for refractive vision correction and particularly to those procedures involving removal of corneal tissue to effect such corrections.

BACKGROUND OF THE INVENTION

Reshaping of the cornea, for refractive vision correction, has been the object of various procedures, some of which have only recently been developed. In one well known procedure (radial keratotomy-RK), the cornea is incised with radial cuts to flatten the anterior surface shape of the cornea in order to correct for myopia. This procedure, is however a surgical one, requiring a high degree of skill and judgment for effective and safe implementation. Additionally, the myopia-corrective flattening is usually not stable, even when properly done, with gradual progression to hyperopia over time.

In other, more recently developed procedures, a preselected portion of the anterior surface of the cornea (i.e. corneal tissue) is removed to change the effective curvature of the cornea with respect to image focusing. The change in cornea curvature is selected to provide the requisite refractive vision correction.

A relatively recently developed excimer laser-based system operates using a photochemical ablation, rather than by cutting. The sequence of incident laser pulses gradually removes the corneal tissue in successive steps. This method known as photo-refractive keratectomy (PRK) is generally safe and effective. However, there are several drawbacks, in addition to the high cost of the equipment, inherent with the PRK procedure. Foremost of the drawbacks is the error factor, or lack of emmetropia, of more than ±0.5 diopters, as compared to the less than ±0.25 diopter error, typical with spectacles or contact lenses. In addition, use of the laser results in a rough corneal surface. In addition, there are long term effects relative to the physiology of the cornea and its interaction with the laser during ablation, which may result in the gradual reversal of the correction or which provide complications due to wound healing and concern about possible mutagenic effects.

The cornea comprises a thin protective epithelium layer on top of the Bowman's membrane or layer, which in turn covers the major corneal stroma. While the epithelium is regenerative, the Bowman's membrane is not. With ablative corneal tissue removal procedures such as PRK, the epithelium and Bowman's membrane are removed together with a portion of the stroma. Subsequently, the epithelium regenerates on the exposed outer surface of the cornea but directly on the stroma, since the Bowman's layer is not regenerated. Direct regrowth of the epithelium on the stroma can however cause an undesirable corneal haze which gradually dissipates over time. PRK has not yet been approved by the FDA for use in the US.

Both RK and PRK, because of inherent instabilities and error factors, are also usually not suitable for correction of myopia of more than −6 diopters and PRK is not currently suitable for corrections other than myopia. A surgical procedure known as Automated Lamellar Keratoplasty (ALK) preserves the Bowman membrane and has been used for corrections of up to −20 diopters. In such procedure there is an initial surgical removal, with a micro-keratome, of a uniform thickness button or lenticule of corneal tissue of a thickness containing the epithelium layer, Bowman's membrane (intact) and a portion of the stroma. The button or lenticule preferably remains hingedly attached at one point to the cornea. The lenticule is moved out of the way, the stroma bed is then surgically reshaped, as required, and the lenticule is replaced, with good adherence and healing of the stroma—stroma surfaces and with the Bowman membrane being preserved, leaving the cornea clear. It appears that the stroma—stroma healing of the ALK procedure reduces, if not eliminates, wound healing instabilities, making this procedure the most suitable for large refractive corrections.

However, despite the advantage of retention of vision clarity and healing stability, the procedure is not very favored since it is complex, requiring high surgical skill, is expensive, is usually inaccurate, with dependency on the surgeon's skill, and it can cause irregular astigmatism. These factors can be attributed to the viscous nature and relatively generally unsupported character of a cornea, in addition to reflexive eye movements, which makes use of a scalpel, or even a micro-keratome, difficult and highly subject to inaccuracies.

It is an object of the present invention to provide a method and device for the highly controlled cutting removal of corneal tissue for refractive correction.

It is a further object of the present invention to provide a method and device for refractive vision correction, which embodies the advantages of the ALK procedures but with enhanced accuracy and reduced complexity.

It is a further object of the present invention to provide such method and device with an accuracy at least comparable to that of spectacles or lenses and wherein the smoothness, polish and clarity of original corneal tissue is substantially retained.

These and other objects, features and advantages will become more evident from the following discussion and the drawings in which:

SHORT DESCRIPTION OF THE DRAWINGS

SUMMARY OF THE INVENTION

Figure 1:
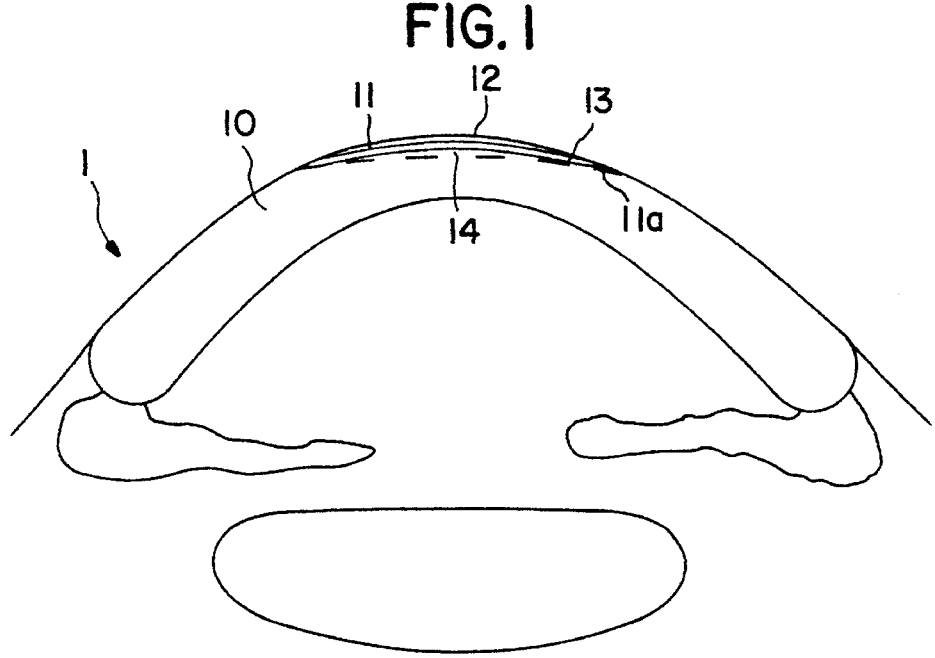
FIG. 1 is a representation of a side cross section view of an eye with the portion of the cornea to be removed, marked off.

Generally the present invention comprises a method and device for the selective, accurate removal of corneal tissue, and change of curvature thereof, for refractive vision correction of an eye.

In accordance with the method of the present invention, the removal is effected by the steps of:

a) determining the dimensions, shape and position of an anterior portion of the corneal tissue which is to be removed to provide the appropriate refractive vision correction;

b) defining a surface, usually curved, along which the corneal tissue is to be cut for removal of the anterior portion of the corneal tissue, to provide the appropriate refractive correction;

c) deforming the anterior portion of the corneal tissue with deformation means whereby the surface to be cut assumes a planar configuration; and d) cutting along the planar surface with cutting means.

The anterior portion, as described above, for removal, also may include corneal stroma tissue which is removed beneath a lenticule or button, as in ALK procedures.

A device for use in effecting the method of the present invention comprises a non-planar template member as the deformation means. The template is adapted specifically to be placed and centered on the anterior portion of the corneal tissue to be removed, whereby it comprises a non-planar surface therein to which the anterior portion, to be removed, is adapted to be fitted and deformed by such fitting.

The deformation is predeterminately controlled, such that the surface to be cut, at the base of this anterior portion assumes a planar configuration, which is accessible for the cutting thereof. The non-planar surface of the template has a height relative to a plane at the base of the template equal to the computed difference, point by point, of the difference in height between the anterior and posterior surfaces of the portion of the corneal tissue which is to be removed. The computed difference also should take into account geometrical distortion and tissue compression. As a result, the posterior surface (i.e. the surface to be cut) assumes a planar configuration. It is noted that cognizance (with some variation of the shape of the template) must be taken of the fact that there is some distortion of the lateral spacing when the posterior surface is flattened to the planar shape without substantial compressing of the cornea.

DETAILED DESCRIPTION OF THE INVENTION

In the initial determination of the dimensions, shape and position of the anterior portion of the corneal tissue (which is to be removed, to provide the appropriate refractive vision correction), the predictable effects of epithelium regrowth and wound healing, on the altered shape, should be taken into account.

For different refractive corrections, a series or set of non-planar templates of appropriately differing shape and dimensions is used, though specifically adapted templates may be readily constructed, if necessary. Templates, including custom-made templates may be made in various ways including porous metal, such as sintered stainless steel, which can be appropriately formed with high accuracy milling techniques, electrostatic discharge machines.

The porous nature of the material is advantageous since it is preferred that the non-planar area into which anterior portion of the cornea is fitted, also functions as a "vacuum chuck" for the portion of the cornea to be removed, in order to ensure complete fitting and positive holding during the cutting step. It is preferred that vacuum suction means of suitable minimal suction strength be provided, through porous walls of the template, e.g. with micron sized pores therein, as formed from materials such as sintered stainless steel, in order to more closely conform and hold the anterior portion therewithin against the non-planar surface thereof.

The shape of the template for a given desired correction depends on the relative position of the cutting plane and it is necessary that these portions be well established. The templates may be sintered stainless steel frits with high porosity exceeding 24% so that they will exhibit suction. Small diameter, glass thin wall tubes in a circular array with ends positioned to establish the template shape are another alternative. Typical template dimensions are 6 mm in diameter, with deviations of the surface from planarity of 150 microns or less. Another alternative is a system of depressions in the template, that are connected to a vacuum.

The cutting means, is most preferably shaped, by a nozzle, high speed rectilinear water (sterile saline solution) jet spray produced by a water pressure of between 3000 to about 20000 psi and typically between 6000 to 8000 psi. The higher the pressure, the greater the speed of the water emitted from the nozzle. A small diameter water jet spray of this character has been shown to provide a very smooth transverse cut in corneal tissue, with a smoothness and polish similar to that of the original tissue surface.

In order to further enhance the accuracy of the method and device of the present invention it is preferred that the water jet spray be emitted with a cross section in the form of a planar cutting sheet whereby a transverse cut can be effected without scanning the water jet relative to the tissue, though a scanning cutting jet is within the scope of the present invention. A suitable dimension of a cutting water jet sheet is about 6 mm by 25 microns. In such embodiment, the water jet is controllably used via a ring member having a partial circumferentially disposed dispensing slit therein. The ring member is adapted to be seated around the template on the cornea and positioned such that the dispensing slit is laterally aligned with the planar cutting surface. After the template is positioned, pulsed activation of the water jet effects a mirror smooth transverse cut of the corneal tissue, held by the template in a fraction of a second. The ring further comprises a secondary opening opposite the slit, for reception and removal of the water of the water jet.

In the preferred embodiment of the present invention, the water jet micro-keratome has two main parts, the cutting ring and the linear water jet beam template and its holder. This micro-keratome is used in the following manner. The vertical meridian and center of the vision axis are identified by means similar to those in use for RK, and marked using a standard tool as used in RK. The cornea is viewed through the operating microscope. The cutting ring is placed on the cornea and centered and positioned relative to the marks on the cornea. Suction is then applied to the cutting ring, thereby positioning it firmly on the cornea. Thereafter the template and its holder are placed into the center of the cutting ring and locked into place. The template and the plane of the cut are thereby juxtaposed in an unambiguous repeatable manner and the cut is made relative to the template.

DETAILED DESCRIPTION OF THE DRAWINGS AND THE PREFERRED EMBODIMENT

With specific reference to the drawings, in FIG. 1, a human eye 1 is shown in schematic cross section. Portion 11 of the cornea 10, marked off with dashed lines, has been calculated and predetermined to be removed for appropriate refractive vision correction. However, the base 11a of the portion to be removed 11, has a curvature, which makes the accurate removal thereof, difficult to control. Portion 11 includes a section of the epithelium 12 and the Bowman's layer 13, as well as a segment of corneal stroma 14.

Figure 2:
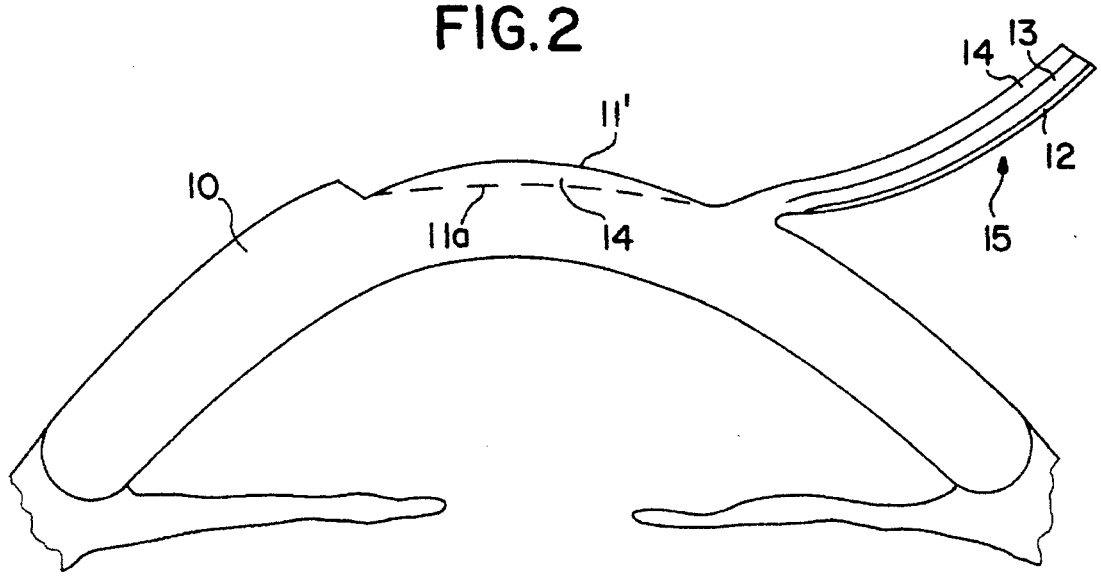
FIG. 2 shows a lenticule of the outer corneal tissue being hingedly formed.

FIG. 2 illustrates the ALK type procedure wherein a lenticular flap 15, of epithelium 12, Bowman's layer 13 and corneal stroma 14 are hingedly moved out of position and cornea 10 is shown with portion to be removed 11', for the refractive vision correction. In this embodiment, portion 11' is comprised only of a segment of the corneal stroma 14, though the base 11a still embodies a curvature.

Figure 3:
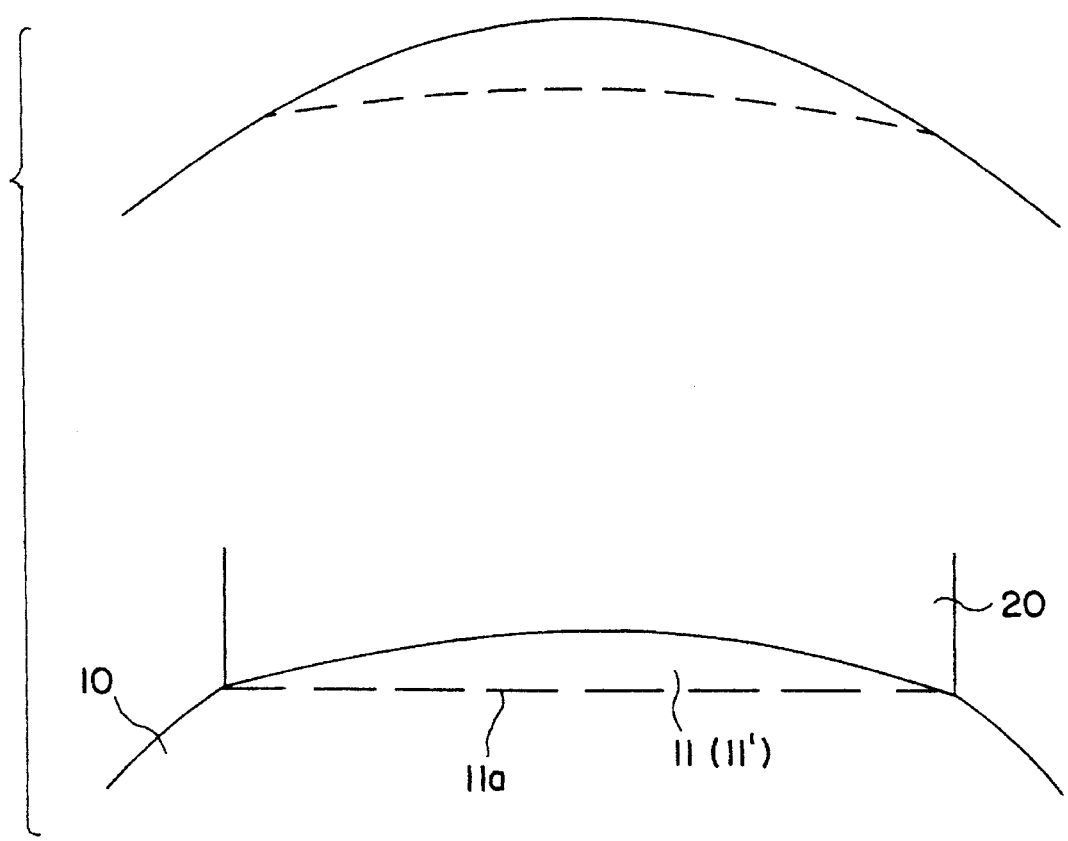
FIG. 3 depicts the placement of the template of the present invention on the portion of the cornea to be removed.
Figure 3A:
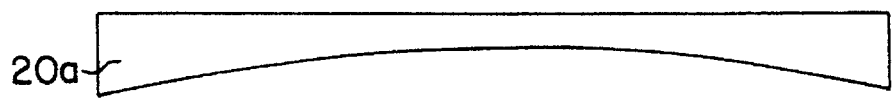
FIGS. 3a, 3b and 3c show, in cross-section, illustrative templates, as used for correction of myopia, hyperopia and astigmatism, respectively.
Figure 3B:
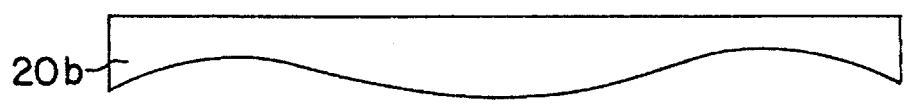
Figure 3C:
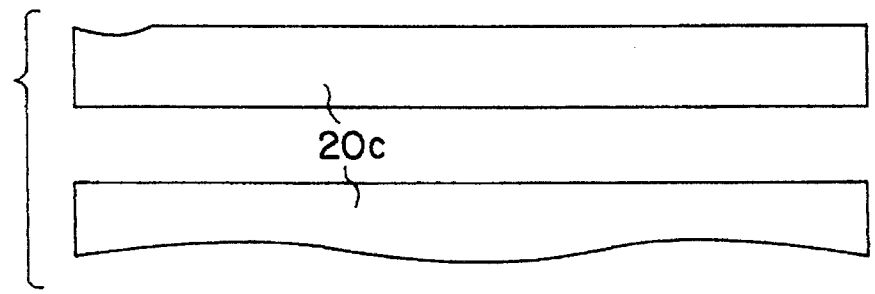
Figure 4:
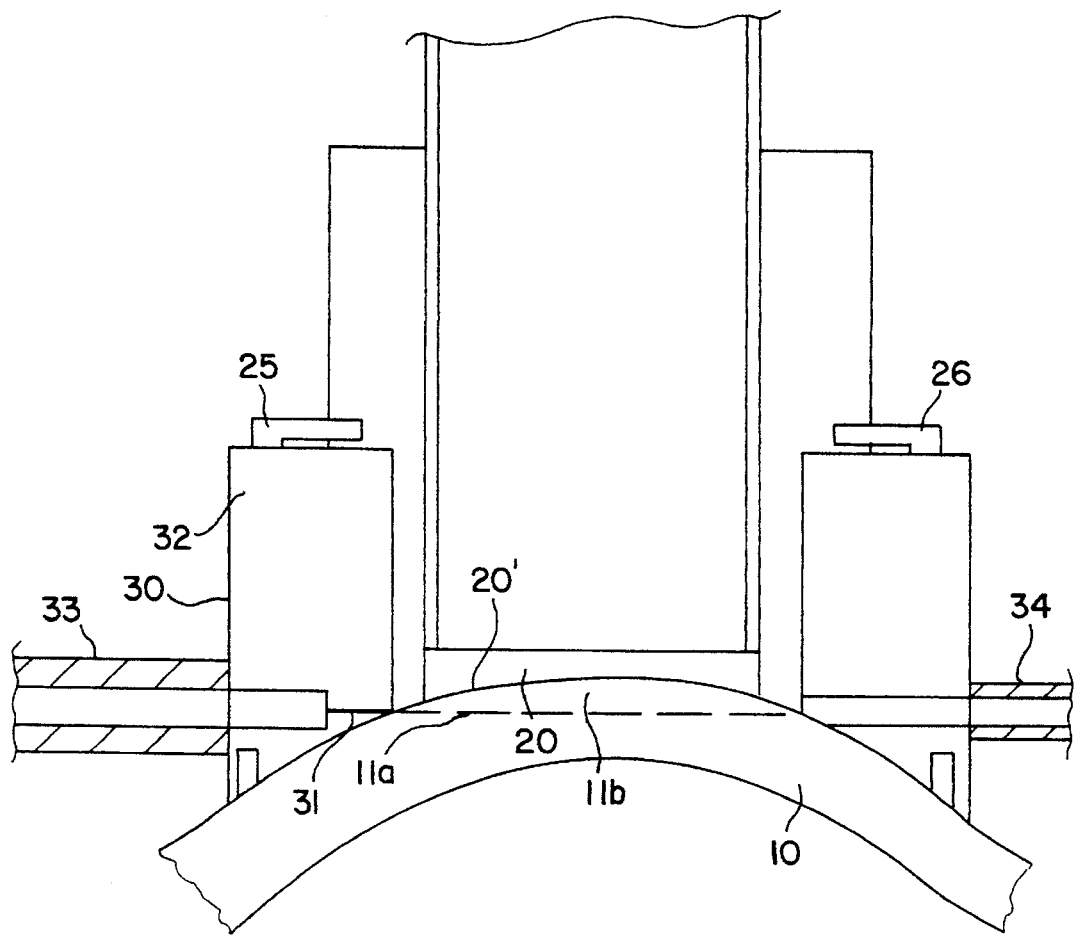
FIGS. 4 and 4a illustrate (side cross section and top view respectively) the use of a water jet and a cutting guide ring relative to the template and the corneal tissue to be removed.

In accordance with the present invention, in FIG. 3, template 20 is applied to either portion 11 or more preferably to portion 11', to deform the portion, on which it is seated, to provide base 11a with a planar surface conformation, suitable for planar cutting as shown in FIG. 4. As shown in cross section in FIGS. 3a–3c respectively, templates 20a–20c, illustrate templates used with: corrections for myopia, with decreased curvature (20a); correction for hyperopia, with increased curvature in the optical zone (20b); and with steepened curvature along the horizontal meridian (20c—shown with vertical and horizontal cross sections) for the correction of astigmatism. In each embodiment the respective template is adapted to the type of correction (myopia, hyperopia, and astigmatism) and to the degree of correction required. The respective templates 20a–c, when fitted, cause the portions, to be removed, to be deformed such that an externally exposed planar surface for cutting is formed, as shown in FIG. 3, at the base of the template.

Figure 4A:
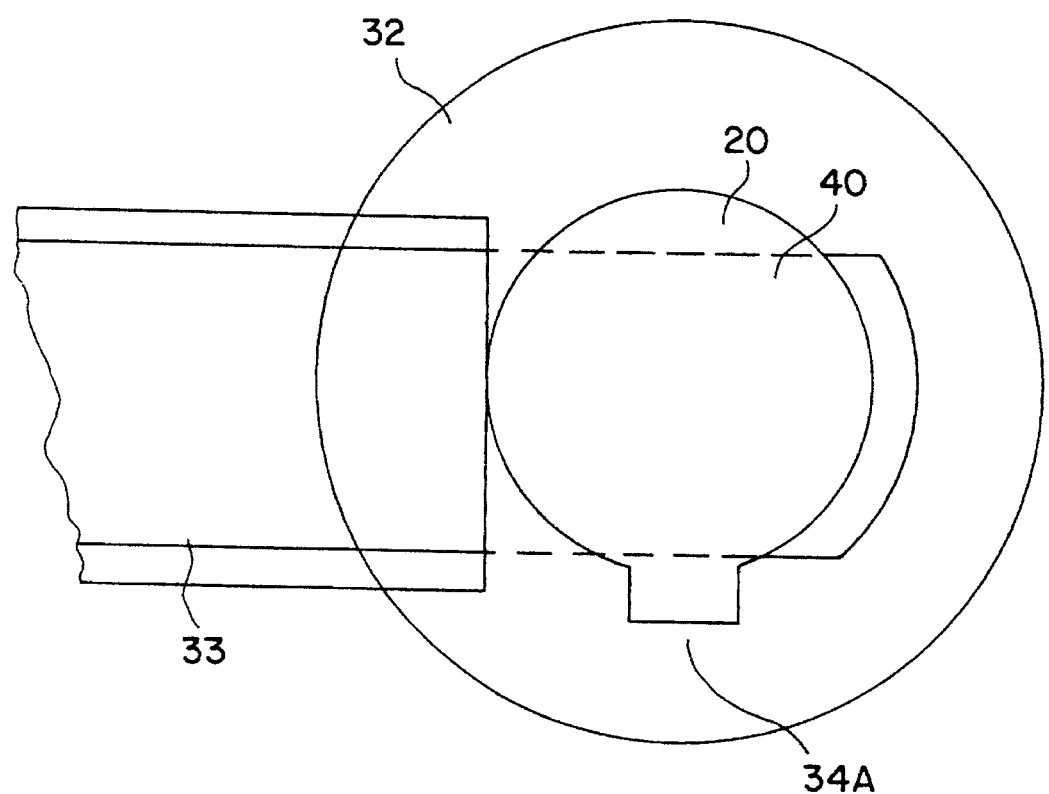

In FIGS. 4 and 4a, template 20, is shown as being positioned on cornea 10. Water jet cutting guide 30, is positioned relative thereto, such that planar surface 11a is exposed and aligned with water jet nozzle 31. The water jet cutting guide 30 is in the form of a ring 32, with water inlet 33, to nozzle 31, and water outlet 34. Template 20 is concentrically placed within the ring 32 and locked into position by locking tabs 25 and 26. To ensure that the deformation is effective in making the planar surface a true surface for cutting (i.e., wherein, after the cutting, the cornea relaxes into the desired configuration), a suction vacuum is applied through the porous template to cause the cornea surface 11b to become closely conformed to template inner surface 20'. The vacuum is maintained at least until the planar surface 11a has been cut. Water jet nozzle 31 is rectilinear in conformation (thin narrow slit) of a width dimension, e.g., 6 mm, suitable to emit a cutting sheet of water 40 at least equal to that of the planar surface 11a. As a result, a single pulse or burst of pulses, of water, without relative movement of nozzle and cornea, accurately cuts the cornea as required, in a very short period of time. Since the cut is planar and is effected by aligned controlled elements, and with the cornea being fully supported during the cutting, accuracy is very high. In addition, the water jet is without heat or abrasive elements. The cut planar surface retains the smoothness and polish of the original corneal tissue.

After the cut is completed, the template and cutting ring are removed from the cornea. If the cut is effected without an ALK procedure, the corneal correction is complete. If an ALK procedure has been utilized (as shown in FIG. 4a, the ring 32 is provided with a keyway 34 to allow hinging of the lenticular flap 15 out of the way of the waterjet blade 40) the hinged lenticule is placed over the cut stroma tissue for healing in accordance with such known procedure.

It is understood that the details contained in the drawings and description are illustrative of the present invention and that changes may be made in procedure and with the devices utilized in effecting the procedure, without departing from the scope of the present invention as defined in the following claims.

What is claimed is:

1. A method for the selective, accurate removal of layers of corneal tissue, and change of curvature thereof, for refractive vision correction of an eye, comprising the steps of:

a) determining dimensions, shape and position of an anterior portion of the corneal tissue which is to be removed to provide an appropriate refractive vision correction;

b) defining an internal surface, along which the corneal tissue is to be cut for removal of the anterior portion of the corneal tissue, to provide the appropriate refractive correction;

c) deforming the anterior portion of the corneal tissue with deformation means whereby the internal surface to be cut assumes a planar configuration; and d) cutting along the planar surface with a micro-keratome comprised of a high speed water jet; and wherein said deformation means comprises a template adapted specifically to be placed and centered on the anterior portion of the corneal tissue to be removed, whereby the template comprises a surface therein to which the anterior portion, to be removed, is adapted to be fitted and deformed by such fitting, the deformation being predeterminately controlled, such that the internal surface to be cut, at the base of the anterior portion assumes a planar configuration, which is accessible for the cutting thereof, beyond an end of the template.

2. The method of claim 1, wherein the refractive correction is for myopia.

3. The method of claim 1, wherein the refractive correction is for hyperopia.

4. The method of claim 1, wherein the refractive correction is for astigmatism.

5. The method of claim 1, wherein said water jet is formed with a pressure between 3000 to 20000 psi.

6. The method of claim 1, wherein said pressure is between 6000 to 8000 psi.

7. The method of claim 1, wherein the anterior portion is defined between anterior and posterior surfaces and wherein the surface of the template has a height relative to a plane at the end of the template equal to the computed difference, point by point, of the difference in height between the anterior and posterior surfaces of the portion of the corneal tissue which is to be removed.

8. The method of claim 7, wherein the anterior portion is conformed to and held at the surface of the template by vacuum suction means.

9. The method of claim 8, wherein the template is comprised of a porous material through which said vacuum suction means is applied.

10. The method of claim 1, wherein said water jet comprises a planar cutting sheet.

11. The method of claim 10, wherein said water jet has a width of up to 6 mm.

12. The method of claim 10, wherein said planar cutting sheet is of a dimension sufficient to effect the cutting of the interior surface without scanning of the water jet and wherein said interior surface is cut with said water jet without scanning.

13. The method of claim 1, wherein a lenticule of uniform thickness, containing the epithelium and Bowman's layer, is removed from the anterior portion prior to said step of defining a surface, along which the corneal tissue is to be cut for removal of the anterior portion of the corneal tissue, to provide the appropriate refractive correction, and wherein said lenticule is replaced on the surface cut with the cutting means.

14. The method of claim 13, wherein the refractive correction is up to −20 diopters.

15. A device for effecting the method of claim 13, comprising a template adapted specifically to be placed and centered on the anterior portion of the corneal tissue to be removed below said lenticule, whereby the template comprises a surface therein to which the anterior portion, to be removed, is adapted to be fitted and deformed by such fitting, the deformation being predeterminately controlled, such that the surface to be cut, at the base of the anterior portion assumes a planar configuration, which is accessible for the cutting thereof, beyond an end of the template, wherein the anterior portion is defined between anterior and posterior surfaces and wherein the surface of the template has a height relative to a plane at the end of the template equal to the computed difference, point by point, of the difference in height between the anterior and posterior surfaces of the portion of the corneal tissue which is to be removed, said device further comprising vacuum suction means adapted to create a suction between the surface and the anterior portion, wherein said cutting means comprises a micro-keratome comprised of a high speed water jet, having a planar sheet configuration, and being formed with a pressure between 3000 to 20000 psi, wherein said device further comprises means to align said water jet with said planar surface for the cutting thereof, said aligning means comprising a ring member supporting said water jet, with said ring member comprises means for being affixed in aligned relation with said template.

16. The device of claim 15, wherein said lenticule remains hinged to the cornea, and wherein the ring member comprises means to permit the hinged lenticule to be moved away from interfering with placement of the template on the cornea.

17. A device for effecting the steps of deforming and cutting in the method of claim 1, comprising a template adapted specifically to be placed and centered on the anterior portion of the corneal tissue to be removed, whereby the template comprises a surface therein to which the anterior portion, to be removed, is adapted to be fitted and deformed by such fitting, the deformation being predeterminately controlled, such that the interior surface to be cut, at the base of the anterior portion, assumes a planar configuration, which is accessible for the cutting thereof, beyond an end of the template, wherein the anterior portion is defined between anterior and posterior surfaces and wherein the surface of the template has a height relative to a plane at the end of the template equal to the computed difference, point by point, of the difference in height between the anterior and posterior surfaces of the portion of the corneal tissue which is to be removed; wherein said device further comprises micro-keratome cutting means comprised of a high speed water jet.

18. The device of claim 17, further comprising vacuum suction means operatively connected to said template and adapted to create a suction between the surface of the template and the anterior portion to effect said fitting and deformation.

19. The device of claim 18, wherein said template is porous and said vacuum suction means is positioned relative thereto to effect a vacuum suction through pores in the porous template to effect said suction.

20. The device of claim 17, wherein said means for forming the water jet forms the water jet having a pressure between 3000 to 20000 psi.

21. The device of claim 17, wherein said device comprises means for forming the water jet into a planar cutting sheet.

22. The device of claim 21, wherein said planar cutting sheet is of a dimension sufficient to effect the cutting of the interior surface without scanning of the water jet.

23. The device of claim 21, wherein said device further comprises means to align said water jet with said planar surface for the cutting thereof.

24. The device of claim 23, wherein aligning means comprises a ring member supporting said water jet, with said ring member comprises means for being affixed in aligned relation with said template.

25. A method for cutting a lenticule of uniform thickness in the corneal tissue of an eye, said lenticule, containing the epithelium and Bowman's layer, is hingedly removable by the steps of:
 a) deforming the anterior portion of the corneal tissue with deformation means whereby an internal surface to be cut assumes a planar configuration parallel to the defomed anterior portion; and
 b) cutting along the planar surface with a micro-keratome comprised of a high speed water jet; and wherein said deformation means comprises a template adapted specifically to be placed and centered on the anterior portion of the corneal tissue to be removed, whereby the template comprises a surface therein to which the anterior portion, to be hingedly removable, is adapted to be fitted and deformed by such fitting, the deformation being predeterminately controlled, such that the internal surface to be cut, at the base of the anterior portion assumes a planar configuration, which is accessible for the cutting thereof, beyond an end of the template.

* * * * *